United States Patent [19]

Ara et al.

[11] Patent Number: 5,147,796
[45] Date of Patent: Sep. 15, 1992

[54] ALKALINE PULLULANASE Y HAVING α-AMYLASE ACTIVITY

[75] Inventors: Katsutoshi Ara, Oyama; Katsuhisa Saeki, Kawachi; Kazuaki Igarashi, Ichikai; Susumu Ito, Utsunomiya, all of Japan

[73] Assignee: Kao Corporation, Tokyo, Japan

[21] Appl. No.: 825,314

[22] Filed: Jan. 27, 1992

Related U.S. Application Data

[63] Continuation of Ser. No. 583,849, Jul. 13, 1990, abandoned.

[30] Foreign Application Priority Data

Sep. 19, 1989 [JP] Japan ................... 1-242605

[51] Int. Cl.$^5$ ............................ C12N 9/44; C12N 1/00
[52] U.S. Cl. ................................... 435/210; 435/832
[58] Field of Search ........................... 435/210, 832

[56] References Cited

U.S. PATENT DOCUMENTS

| | | | |
|---|---|---|---|
| 3,622,460 | 11/1971 | Masuda et al. | 435/210 |
| 3,963,575 | 6/1976 | Balich | 435/210 |
| 4,318,989 | 3/1982 | Marshall | 435/210 |
| 4,628,028 | 12/1986 | Katkocin et al. | 435/210 |
| 4,628,031 | 12/1986 | Zeikus et al. | 435/210 |
| 4,657,865 | 4/1987 | Takasaki et al. | 435/210 |
| 4,734,364 | 3/1988 | Line et al. | 435/210 |
| 4,902,622 | 2/1990 | Nakai et al. | 435/210 |

FOREIGN PATENT DOCUMENTS 258050 3/1988 European Pat. Off. ............ 435/210

OTHER PUBLICATIONS

*Enzyme Nomenclature*, pp. 314 and 315, 1984.
Fems Microbiology Letters, vol. 20, 1983, pp. 55–59, Elsevier; C. T. Kelly et al.: "Extracellular alpha-glucosidase of an alkalophillic microorganism Bacillus sp. ATCC 21592" *p. 55, summary; pp. 57–58, paragraph: Results and discussion*.
Biochimica et Biophysica Acta, vol. 397, 1975, pp. 188–193, Elsevier Scientific Publishing Co., Amsterdam, NL; N. Nakamura et al.: "Purification and some properties of alkaline pullulanase from a strain of bacillus No. 202-1, an alkalophillic microorganism".

*Primary Examiner*—Douglas W. Robinson
*Assistant Examiner*—Mike Meller
*Attorney, Agent, or Firm*—Oblon, Spivak, McClelland, Maier & Neustadt

[57] ABSTRACT

An isolated alkaline pullulanase Y having α-amylase activity; a microorganism producing the alkaline pullulanase Y; and a process for producing the alkaline pullulanase Y are disclosed. The alkaline pullulanase Y having α-amylase activity has its optimum pH at higher alkaline range than conventional alkaline pullulanases and exhibits excellent stability in a wide pH range. Further, the alkaline pullulanase Y has strong resistance to almost all detergent components such as surfactants, chelating agents, proteases for detergents, and the like. Thus the alkaline pullulanase Y can advantageously be used as a detergent component.

1 Claim, 6 Drawing Sheets

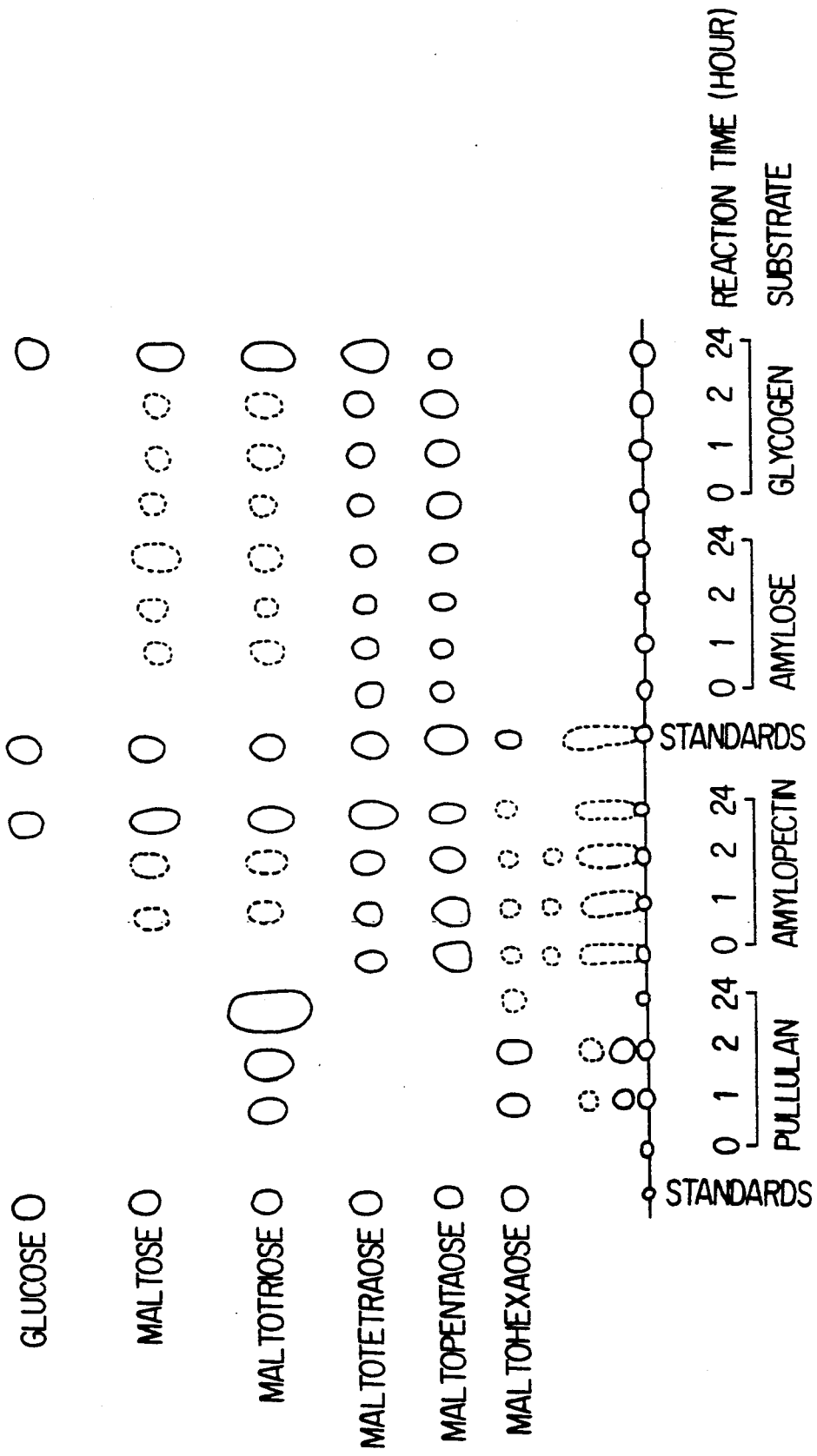

ALKALINE PULLULANASE Y HAVING α-AMYLASE ACTIVITY

This application is a continuation of application Ser. No. 07/583,849, filed on Sep. 13, 1990, now abandoned.

BACKGROUND OF THE INVENTION

1. Field of the Invention

This invention relates to a novel alkaline pullulanase Y having an α-amylase activity, a microorganism producing said alkaline pullulanase Y, and a process for producing said alkaline pullulanase Y.

2. Description of the Background Art

Pullulanase is an enzyme which breaks only α-1,6-glycosidic linkage of pullulan and finally produces maltotriose. Pullulanase was first discovered from a strain belonging to *Aerobacter aerogenes* by Bender and Wallenfels in 1961 [Biochem. Z., 334, 79, (1961)]. Recently, various microorganisms capable of producing pullulanase have been reported. These microorganisms are, for example, *Bacillus sp.* [J. Jpn. Soc. Starch Sci., 30, 200, (1983)]; *Bacillus acidopullulyticus* [Agric. Biol. Chem. 52, 2293, (1984)]; *Bacillus stearothermophilus* [Eur. J. Appl. Microbiol. Biotechnol., 17 24 (1983); *Streptococcus mitis* [Biochem. J., 108, 33, (1968)]; Lactobacillus [Denpun Kagaku, 28, 72, (1981)]; *Clostridium sp.* [Appl. Environ. Microb., 53, 7, (1987)]; *Clostridium thermohydrosulfuricum* [Appl. Environ. Microb., 49, 5, (1985), J. Bacteriol., 164, 3, (1985), Biochem. J., 246, (1987)], *Thermus aquaticus* [Enzyme Microb. Technol., 8, (1986]); and Thermus sp. [J. Jpn. Soc. Starch Sci., 34, 1 (1987)].

It is known that pullulanase not only possesses activities against pullulan, but also hydrolysis activities against α-1,6-glycosidic linkage of starch, glycogen, amylopectin, as well as against branched oligosaccharides produced by their partial decomposition. Because of this characteristic, pullulanase is called a "debranching enzyme".

Further, it has been found that pullulanase used in combination with both endo-type amylase and exo-type amylase could yield glucose or maltooligo-saccharides such as maltose, maltotriose, maltotetraose, maltopentaose, or maltohexaose from starch in a high yield. This characteristic has lately attracted considerable attention.

In addition, development of pullulanase having α-amylase activity capable of reacting with an α-1,4-glycosidic linkage has been desired in order to simplify the conventional sugar-manufacturing processes in which two or more of enzymes are being used. In this respect, only two enzymes have been reported. One is a combined enzyme of pullulanase-amylase produced by *Bacillus subtilis* TU (Agric. Biol. Chem., 51, 9, (1987); Japanese Patent Publication No. 18717/1989) and the other is an amylase having pullulanase activity produced by *Bacillus circulans* (Japanese Patent Laid-open No. 60376/1989).

Meanwhile, it has been elucidated that the combined use of a pullulanase having the above-mentioned characteristics together with an α-amylase as additives for dish-washing detergents or laundry detergents remarkably improves detergency against mainly starch soil (Japanese Patent Application No. 285424/1988). Further utilization of pullulanase is expected in these fields.

However, almost all naturally occuring pullulanases are classified into neutral or acidic pullulanases which exhibit the maximum and stable enzymatic activity in neutral or acidic conditions. There exists few alkaline or alkali-resistant pullulanases having a better stability and exhibiting the maximum activity at an alkaline pH range at which cloth-washing or dish-washing is performed. As for an alkaline pullulanase having α-amylase activity, such a kind of alkaline pullulanase has never been discovered until now. An alkaline pullulanase herein denotes that having an optimum pH at an alkaline range. An alkali-resistant pullulanase denotes that having an optimum pH in a neutral to acidic range, but having a sufficient degree of activities in an alkaline range as it has at its optimum pH while retaining a good stability. The word "neutral" herein are defined as a pH range of 6-8 and the word "alkaline" designates a pH range of not less than 8.

No processes for producing alkaline pullulanase nor alkali-resistant pullulanase is heretofore known, except for a report of Horikoshi et al., which discloses a process for producing alkali pullulanase through culturing an alkalophilic microorganism belonging to genus Bacillus [Biochem, Biophys. Acta, 397, 188, (1975), and Japanese Patent Publication No. 27786/1978).

Pullulanase of Horikoshi et al. is an enzyme having its optimum pH at an alkaline range and possessing wider substrate specificity than conventionally known pullulanases. However, since its optimum pH is in a weak alkaline range of 8-9 and lacks in α-amylase activity, it is not applicable to detergent compositions. In addition, the pullulanase of Horikoshi et al. has a disadvantage that the enzyme is unstable and the productivity of enzyme is low. This type of process is therefore unsuitable for industrial fermentative production. Because of these reasons, the development of pullulanases having an optimum pH in higher alkaline range and having α-amylase activity as well has been desired.

Dish-washing or cloth-washing is usually carried out in a wide pH range of from neutral to high alkaline range. It is therefore worthwhile to discover and obtain natural microorganisms having an optimum pH at highly alkaline range and capable of producing alkaline pullulanase having α-amylase activity which functions as an enzyme usable for dish-washing and cloth-washing detergents.

In view of this situation, the present inventors have carried out extensive studies in order to obtain natural microorganisms capable of producing alkaline pullulanase having α-amylase activity, and, as a result, found that an alkalophilic microorganism Bacillus sp. KSM-AP1378 (FERM P-10886) which was discovered by the inventors in the soils in Tochigi-shi, Tochigi-ken, Japan, was capable of producing a novel alkaline pullulanase Y having α-amylase activity which was effective as a detergent component for automatic dishwasher or for a laundry detergents. This finding has led to the completion of the present invention.

SUMMARY OF THE INVENTION

Accordingly, an object of this invention is to provide a novel alkaline pullulanase having α-amylase activity possessing the following enzymological characteristics:

(1) Action

Acts on pullulan and soluble starch to produce mainly maltotriose from pullulan and mainly maltotetraose and maltopentaose from soluble starch. Acts also on glycogen to produce maltotetraose and maltopentaose.

(2) Substrate specificity

Acts on pullulan, soluble starch, and glycogen.

(3) Working pH and optimum pH range

Has an active pH range on pullulan of 5-12 with an optimum pH range being 8.5-10. Has an active pH range on soluble starch of 4-12 with an optimum pH range being 7-9.5.

(4) pH stability

Is stable in a pH range of 6-10.5 against pullulan and in a pH range of 4-12 against soluble starch (treating condition: 45° C., 10 minutes).

(5) Working temperature and optimum temperature

Acts on pullulan and soluble starch at wide temperatures ranging from 10° to 65° C. with an optimum temperature being 50° C.

(6) Thermal stability

Is stable up to 45° C. when treated in a 10 mM glycine-NaCl-NaOH buffer (pH 9.5) for 30 minutes.

(7) Molecular weight

About 200,000±5,000, when measured by means of electrophoresis using sodium dodecylsulfate (SDS).

(8) Effects of metal ions

Pullulanase activity is adversely affected by $Hg^{2+}$, $Mn^{2+}$, and $Pb^{2+}$ ions and α-amylase activity is adversely affected by $Hg^{2+}$, $Mn^{2+}$, $Pb^{2+}$, $Zn^{2+}$, and $Cd^{2+}$ ions.

Another object of the present invention is to provide a microorganism producing an alkaline pullulanase having α-amylase activity with the above-mentioned characteristics.

Further object of the present invention is to provide a process for producing an alkaline pullulanase having the above characteristics.

Other objects, features and advantages of the invention will hereinafter become more readily apparent from the following description.

BRIEF DESCRIPTION OF THE DRAWINGS

FIG. 1 is a paper chromatography showing the production of maltooligosaccharides when performing enzymatic reaction using the alkaline pullulanase Y having α-amylase activity of the present invention and, as a substrate, pullulan, amylopectin, amylose, and glycogen.

DETAILED DESCRIPTION OF THE INVENTION AND PREFERRED EMBODIMENTS

Figure 2A:
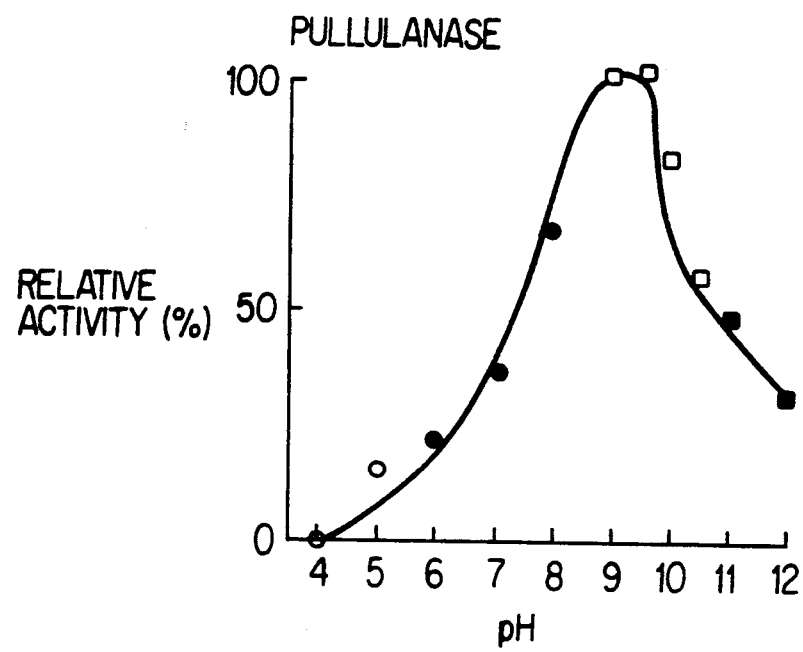
FIGS. 2(a) and 2(b) are drawings showing the relation of reaction pH vs. relative activity of the alkaline pullulanase Y having α-amylase activity of this invention.

Mycological characteristics of a microorganism producing alkaline pullulanase of the present invention is now discussed. The following culture media of 21 sorts (Media 1 to 21) are used for the classification of strains. They all contain 0.5% by weight of sterilized sodium carbonate ($Na_2CO_3$).

COMPOSITIONS OF THE CULTURE MEDIA USED (% BY WEIGHT)

Medium 1: nutrient broth, 0.8; agar powder (manufactured by Wako Pure Chemical Co.), 1.5

Medium 2: nutrient broth, 0.8

Medium 3: nutrient broth, 0.8; gelatin, 20.0; agar powder (manufactured by Wako Pure Chemical), 1.5

Medium 4: Bacto litmus milk, 10.5

Medium 5: nutrient broth, 0.8; $KNO_3$, 0.1

Medium 6: Bacto peptone, 0.7; NaCl, 0.5; glucose, 0.5

Medium 7: SIM agar medium (manufactured by Eiken Kagaku), an amount indicated

Medium 8: TSI agar (manufactured by Eiken Kagaku), an amount indicated

Medium 9: yeast extract, 0.5; Bacto peptone, 1.5; $K_2HPO_4$, 0.1; $MgSO_4.7H_2O$, 0.02; soluble starch, 2.0; agar powder (manufactured by Wako Pure Chemical), 1.5

Medium 10: Koser's medium (manufactured by Eiken Kagaku), an amount indicated

Medium 11: Christensen's medium (manufactured by Eiken Kagaku), an amount indicated Medium 12: the medium including the following compositions (1) and (2) to which added are nitrogen sources consisting of sodium nitrate, sodium nitrite, ammonium chloride, and ammonium phosphate in an amount of 0.25%, 0.2025%, 0.158%, and 0.195% by weight respectively in the medium.

(1) yeast extract, 0.05; $Na_2SO_4$, 0.1; $KH_2PO_4$, 0.1; glucose, 1.0

(2) yeast extract, 0.05; $Na_2SO_4$, 0.1; $KH_2PO_4$, 0.1; glucose, 1.0; $CaCl_2.2H_2O$, 0.05; $MnSO_4.4-6H_2O$, 0.01; $FeSO_4.7H_2O$, 0.001; $MgSO_4.7H_2O$, 0.02

Medium 13: King A medium "Eiken" (manufactured by Eiken Kagaku), an amount indicated Medium 14: King B medium "Eiken" (manufactured by Eiken Kagaku), an amount indicated Medium 15: urea medium "Eiken" (manufactured by Eiken Kagaku), an amount indicated Medium 16: cytochrome-oxidase test filter paper (manufactured by Nissui Pharmaceutical Co., Ltd.)

Medium 17: 3% aqueous hydrogen peroxide

Medium 18: Bacto peptone, 0.5; yeast extract, 0.5; $K_2HPO_4$, 0.1; glucose, 1.0; $MgSO_4.7H_2O$, 0.02

Medium 19: Bacto peptone, 2.7; NaCl, 5.5; $K_2HPO_4$, 0.3; glucose, 0.5; bromthymol blue, 0.06; agar powder (manufactured by Wako Pure Chemical), 1.5

Medium 20: $(NH_4)_2HPO_4$, 0.1; KCl, 0.02; $MgSO_4.7H_2O$, 0.02; yeast extract, 0.05; sugar, 1.0

Medium 21: casein, 0.5; yeast extract, 0.5; glucose, 1.0; $K_2HPO_4$, 0.1; $MgSO_4.7H_2O$, 0.02; agar powder (manufactured by Wako Pure Chemical), 1.5

MYCOLOGICAL CHARACTERISTICS (1) Observation Under Microscope

Cells are rods of a size of 0.8-2.4 μm × 1.8-4.0 μm, with an elliptical endospore (1.0-1.2 μm × 1.2-1.4 μm)

forming at their subterminals. They have flagella and are motile. Gram's staining is indeterminable. Acid fastness: negative (2) Growth in Various Culture Media (a) Nutrient Agar Plate (Medium 1)
Growth of cells is good. Colony has a circular shape, with its surface being smooth and its peripheral end being smooth. The color of the colony is yellow, semitransparent, and glossy.

(b) Nutrient Agar Slant Culture (Medium 1)
Cells can grow. Colony has a cloth-spreading shape, with a color of the colony being glossy, yellow, and semitransparent.

(c) Nutrient Broth (Medium 2)
Cells can grow.

(d) Stab Culture in Nutrient Broth-Gelatin (Medium 3)
Growth of cells is good. Liquefaction of gelatin is observed.

(e) Litmus Milk Medium (Medium 4)
Milk coagulation and peptonization are not observed. Litmus discoloration is indeterminable because the medium is an alkaline medium.

(3) Physiological Characteristics (a) Nitrate Reduction and Denitrification (Medium 5)
Nitrate reduction: positive Denitrification: negative (b) MR Test (Medium 6)
Indeterminable because the medium is an alkaline medium.

(c) V-P Test (Medium 6)
Negative (d) Production of Indole (Medium 7)
Negative (e) Production of Hydrogen Sulfide (Medium 8)
Negative (f) Hydrolysis of Starch (Medium 9)
Positive (g) Utilization of Citric Acid (Medium 10, Medium 11)
Negative in Koser's medium (Medium 10) and indeterminable in Christensen's medium (Medium 11)

(h) Utilization of Inorganic Nitrogen Sources (Medium 12)
Nitrate, ammonium salts, and nitrite are all utilized.

(i) Discoloration (Medium 13, Medium 14)
Negative (j) Urease (Medium 15)
Negative (k) Oxidase (Medium 16)
Negative (l) Catalase (Medium 17)
Positive (m) Growth Range (Medium 18)
Growth temperature: 20°–40° C.,
Optimum growth temperature: 30°–35° C.
Growth pH range: 7–10.5
Optimum pH: 10

(n) Behavior on Oxygen
Aerobic (o) O-F Test (Medium 19)
Discoloration is indeterminable because the medium is an alkaline medium. Cells can grow only in an aerobic condition.

(p) Sugar Utilization (Medium 20)
L-Arabinose, D-xylose, D-glucose, D-mannose, D-fructose, D-galactose, maltose, sucrose, lactose, trehalose, D-sorbitol, D-mannitol, inositol, glycerol, starch, raffinose, salicin, D-ribose, and dextrin are utilized.

(q) Growth in a Medium Containing Sodium Salt (a modification of Medium 1)
Cells can grow in the presence of a 7% of sodium chloride, but can not grow in the presence of a 10% sodium chloride.

(r) Hydrolysis of Casein (Medium 21)
Positive

Based on the above mycological characteristics, the strain of the present invention was examined referring to Bergey'Manual of Determinative Bacteriology, Vol 8 and "The Genus Bacillus" Ruth, E. Gordon, Agriculture Handbook No. 427, Agricultural Research Service, U.S. Department of Agriculture Washington D.C., (1973), and determined as a sporogenous rod-shaped microorganism belonging to the genus Bacillus. The strain does not grow in a neutral range, but can grow mostly in a highly alkaline range. From this fact, the strain of the present invention is classified as an alkalophilic microorganism which was demonstrated by Horikoshi and Akiba [Alkalophilic Microorganism, Japan Scientific Society Press (Tokyo), 1982]. The strain of the present invention is distinguished from a group of microorganisms belonging to genus Bacillus which grows in neutral pH range.

The strain of the present invention, other than the above characteristics, has mycologically different characteristics from those of any conventionally known "alkalophilic Bacillus". Accordingly, the strain of the present invention was determined as a novel strain and named Bacillus sp. KSM-AP1378, which was deposited with Fermentation Research Institute, Agency of Industrial Science and Technology as FERM P-10886.

The production of alkaline pullulanase having $\alpha$-amylase activity of the present invention can be processed by inoculating the microorganisms of the present invention and culturing the microorganisms according to conventional culturing methods. It is desirable to add a suitable amount of carbon and nitrogen sources which the microorganism can utilize in the medium. There are no specific limitations as to the carbon and nitrogen sources. Enumerated as nitrogen sources are organic nitrogen sources such as corn gluten meal, soybean flour, corn steep liquor, casamino acid, yeast extract, pharma media, meat extract, tryptone, soytone, hypro, ajipower, soybean meal, cotton seed meal, cultivator, ajipron, zest, and the like; and inorganic nitrogen sources are such as ammonium sulfate, ammonium nitrate, ammonium phosphate, ammonium carbonate, sodium nitrate, ammonium acetate, and the like. Given as examples of carbon sources are soluble starch, insoluble starch, amylopectin, glycogen, pullulan, and branched oligomers produced by their partial decomposition, and utilizable carbon sources such as glucose, maltose, arabinose, xylose, ribose, mannose, fructose, galactose, sucrose, lactose, trehalose, mannitol, sorbitol, glycerol, and utilizable organic acids such as citric acid, acetic acid and the like. In addition to these carbon and nitrogen sources, inorganic ions such as phosphate, magnesium, calcium, manganese, zinc, cobalt, sodium, potassium, and the like, as required, other micro-nutritious organic or inorganic substances can be added into the culture medium.

A preferable culturing temperature range is 20°–40° C., most preferably 30°–35° C. A preferable pH range is 8–10.5 with a most preferable pH being 10. In this condition, the culturing is usually completed in 2–3 days.

The alkaline pullulanase Y having an α-amylase activity of the present invention can be prepared from the culture broth by means of conventional collection and purification methods applied to general enzymes. Specifically, cells are separated from the culture broth by means of conventional solid-liquid separation methods, such as, centrifugation, filtration, or the like, to obtain a crude enzyme liquid. Although it is possible to use the crude enzyme liquid thus obtained as is, they can be served as a purified enzyme, as required after separating by means of separation methods, e.g. salting out, precipitation, ultrafiltration, and the like, to obtain a crude enzyme, and purifying and crystallizing the crude enzyme by conventional methods.

A preferably method for producing the alkaline pullulanase Y of this invention is now discussed. Strains of an alkalophilic microorganism belonging to the genus Bacillus, for example, strains of KSM-AP1378, are aerobically shake-cultured at 30° C. for three (3) days in a medium containing 1% by weight of pullulan; 1% by weight of polypeptone, 0.5% by weight of yeast extract; 0.1% by weight of $KH_2PO_4$; 0.25% by weight of $Na_2HPO_4 \cdot 12H_2O$; 0.02% by weight of $MgSO_4 \cdot 7H_2O$; and 0.5% by weight of sodium carbonate. Cells are removed from the culture liquid and obtain a supernatant. The supernatant is then purified by means of DEAE cellulose adsorption, α-cyclodextrin affinity chromatography, DEAE Toyopeal (manufactured by Tosoh) chromatography, and Sephacryl (manufactured by Pharmacia) chromatography. A purified enzyme thus obtained gives a single band when it is subjected to electrophoresis using polyacrylamide gel (gel concentration: 15% w/v) and electrophoresis using sodium dodecylsulfate (SDS). In this process, the yield of active pullulanase is approximately 2%.

Enzymological characteristics of a novel enzyme, the alkaline pullulanase Y of this invention are now discussed. Enzymatic activities were measured using the following buffer solutions (50 mM each) according to the method explained below.

The buffer solutions:
pH 4–6: acetate buffer
pH 6–8: phosphate buffer (for measuring pullulanase activity)
pH 6–8: Tris-malate buffer (for measuring α-amylase activity)
pH 8–11: glycine-NaCl-NaOH buffer
pH 11–12: KCl-NaOH buffer

MEASUREMENT OF ENZYMATIC ACTIVITY (1) Pullulanase Activity 0.1 ml of enzyme solution was added to 0.9 ml of each substrate solution prepared from each buffer solution containing pullulan (final concentration in the reaction system: 0.25% w/v) and the mixture was reacted at 40° C. for 30 minutes. After the reaction, reducing sugars were quantitatively determined by means of the 3,5-dinitro-salicylic acid (DNS) procedure. Specifically, 1.0 ml of a DNS reagent was added to 1.0 ml of reaction mixture and the mixture was heated at 100° C. for 5 minutes to develop a color. After cooling, the mixture was diluted by adding 4.0 ml of deionized water. This solution was subjected to colorimetric quantitative analysis at a wave length of 535 nm. One unit (1 U) of enzyme activity was defined as the amount of enzyme which released 1 μmol of reducing sugar (as glucose) per minute under the standard assay conditions.

(2) α-Amylase Activity 0.1 ml of enzyme solution was added to 0.9 ml of each substrate solution prepared from each buffer solution containing soluble starch (final concentration in the reaction system: 0.25% w/v) and the mixture was reacted at 50° C. for 15 minutes. After the reaction, reducing sugars were quantitatively determined by means of a DNS method. Specifically, 1.0 ml of a DNS reagent was added to 1.0 ml of reaction mixture and the mixture was heated at 100° C. for 5 minutes to develop a color. After cooling, the mixture was diluted by adding 4.0 ml of deionized water. This solution was subjected to colorimetric quantitative analysis at a wave length of 535 nm. One unit (1 U) of enzyme activity was defined as the amount of enzyme which released 1 μmol of reducing sugar (as glucose) per minute under the standard assay conditions.

ENZYMOLOGICAL CHARACTERISTICS (1) Action

Acts on pullulan and soluble starch to produce mainly maltotriose from pullulan and mainly maltotetraose and maltopentaose from soluble starch. Acts also on glycogen to produce maltotetraose and maltopentaose. (See FIG. 1)

(2) Substrate Specificity

Acts on pullulan, soluble starch, and glycogen. (See Table 1)

TABLE 1

| Substrate | Concentration | Relative Activity (%) |
|---|---|---|
| Pullulan | 0.25% w/v | 100 |
| Glycogen (oyster) | 0.5% w/v | 25 |
| Glycogen (rabbit liver) | 0.5% w/v | 24 |
| Amylopectin | 0.5% w/v | 55 |
| Amylose | 0.5% w/v | 28 |
| Maltose | $1 \times 10^{-2}$M | 0 |
| Maltotriose | $1 \times 10^{-2}$M | 0 |
| Panose | $1 \times 10^{-2}$M | 0 |
| Isomaltose | $1 \times 10^{-2}$M | 4 |
| Isomaltotriose | $1 \times 10^{-2}$M | 11 |
| Gentiobiose | $1 \times 10^{-2}$M | 0 |

(3) Working pH and Optimum pH Range

The active pH range on pullulan is 5–12 with an optimum pH range being 8.5–10.

Pullulanase activities at various pH were measured using each reaction system consisting of 0.25% w/v of pullulan and a buffer solution of 10 mM acetate (pH 4–5) phosphate (pH 6–8), glycine-NaCl-NaOH (pH 9–10.5), and KCl-NaOH (pH 11–12). Each reaction was carried out at 40° C. for 30 minutes. The results are shown in FIG. 2(a).

Figure 2B:
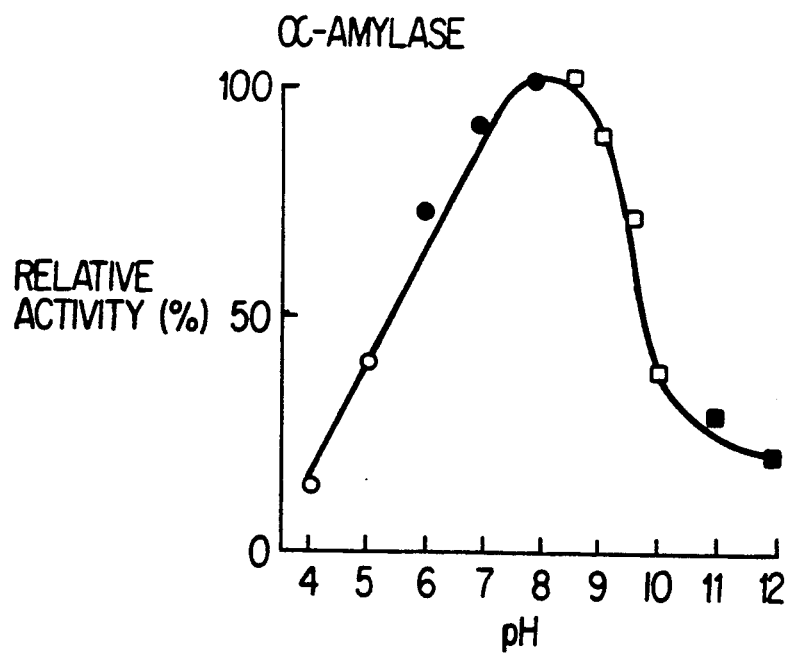

The active pH range on soluble starch is 4–12 with an optimum pH range being 7–9.5.

α-amylase activities at various pH were measured using each reaction system consisting of 0.25% w/v of soluble starch and a buffer solution of 10 mM acetate (pH 4–5), Tris-malate (pH 6–8), glycine-NaCl-NaOH (pH 9–10.5), and KCl-NaOH (pH 11–12). Each reaction was carried out at 50° C. for 15 minutes. The results are shown in FIG. 2(b).

(4) pH Stability

Is stable in a pH range of 6–10.5 against pullulan.

Figure 3A:
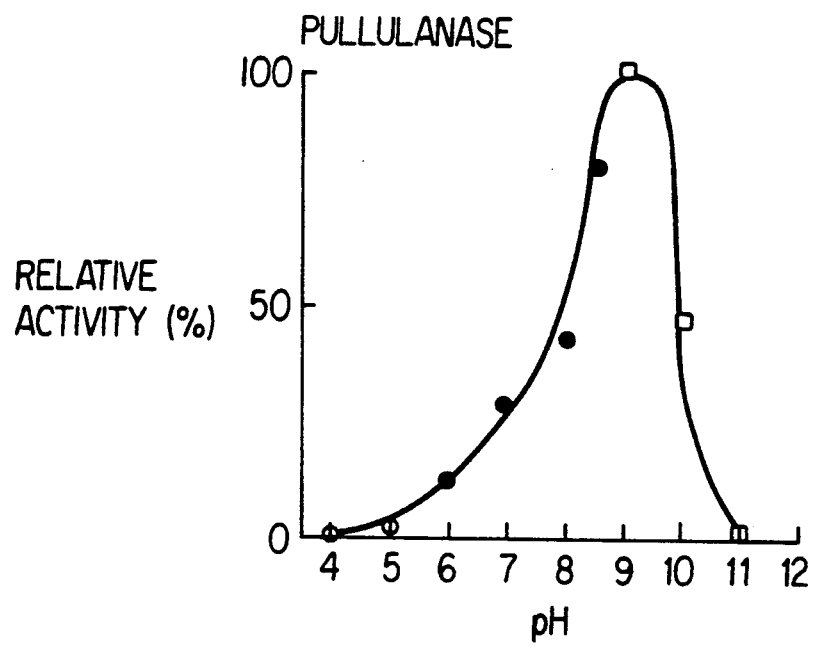
FIGS. 3(a) and 3(b) are drawings showing the relation of pH vs. residual activity of the alkaline pullulanase Y having α-amylase activity of this invention.

Pullulanase activities at various pH were measured using each reaction system consisting of 0.25% w/v of pullulan and a buffer solution of 10 mM acetate (pH 4–5), phosphate (pH 6–8), glycine-NaCl-NaOH (pH 9–10.5), and KCl-NaOH (pH 11–12). Each reaction was carried out at 40° C. for 10 minutes. The results are shown in FIG. 3(a).

Figure 3B:
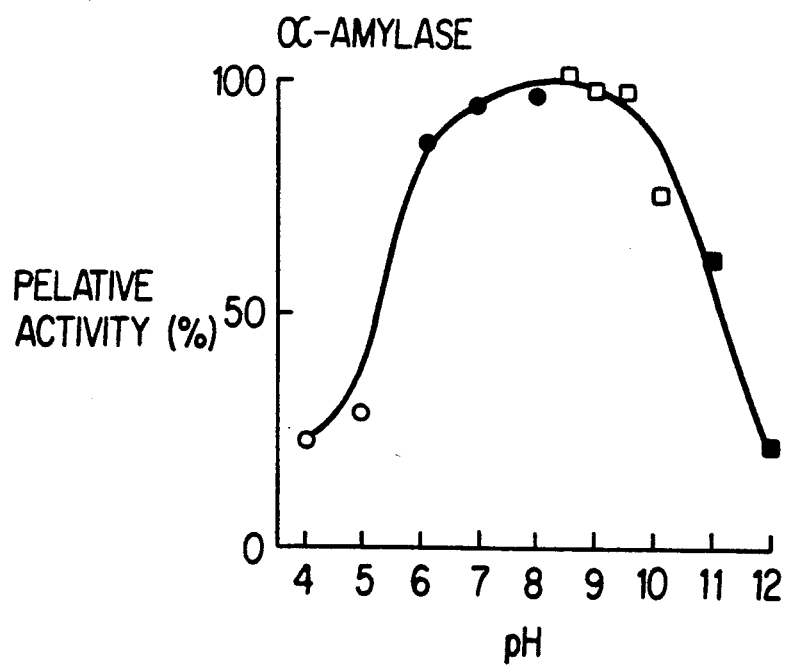

Is stable in a pH range of 4–12 against soluble starch.

α-amylase activities at various pH were measured using each reaction system consisting of 0.25% by weight of soluble starch and a buffer solution of 10 mM acetic acid (pH 4–5), Tris-malate (pH 6–8), glycine-NaCl-NaOH (pH 9–10.5), and KCl-NaOH (pH 11–12). Each reaction was carried out at 50° C. for 15 minutes. The results are shown in FIG. 3(b).

(5) Working Temperature and Optimum Temperature

Figure 4A:
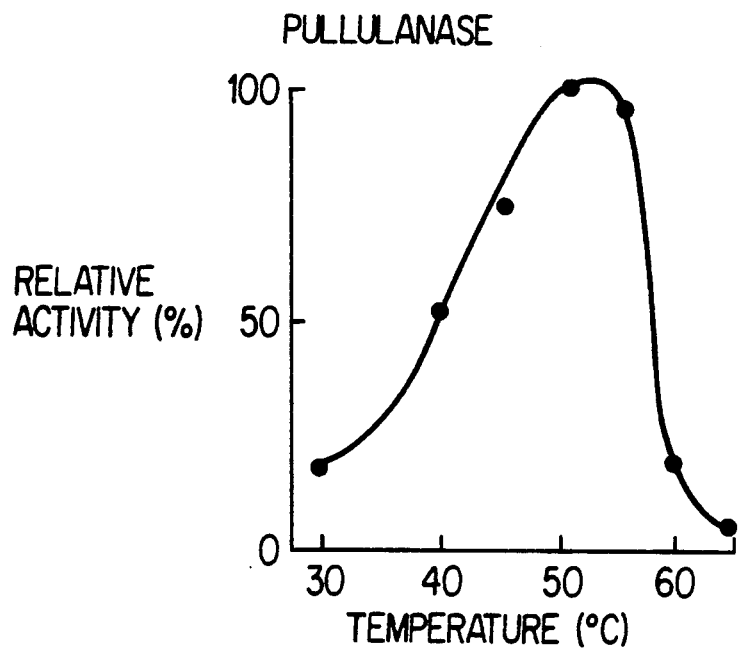
FIGS. 4(a) and 4(b) are drawings showing the relation of reaction temperature (at pH 9.5) vs. relative activity of the alkaline pullulanase Y having α-amylase activity of this invention.
Figure 4B:
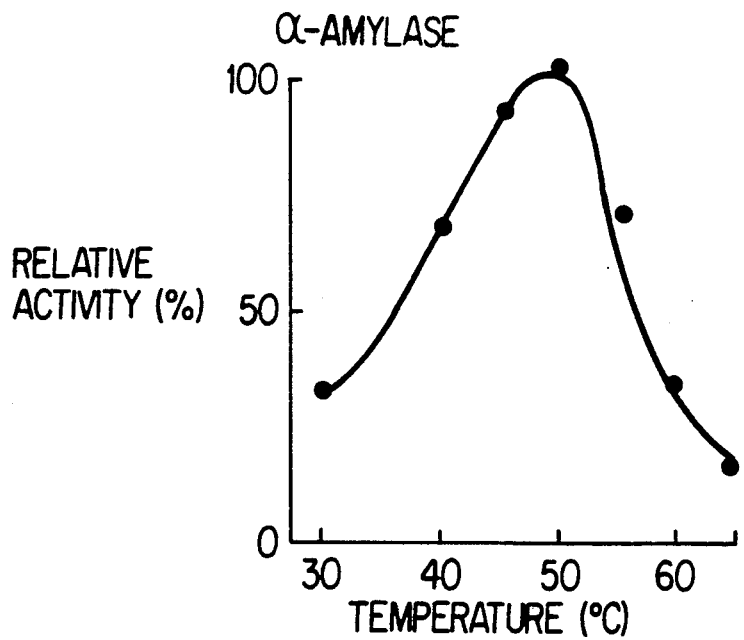

Acts on pullulan and soluble starch at wide temperatures ranging from 10° to 65° C. with an optimum temperature being 50° C. The results are shown in FIGS. 4(a) and 4(b).

(6) Thermal Stability

Figure 5A:
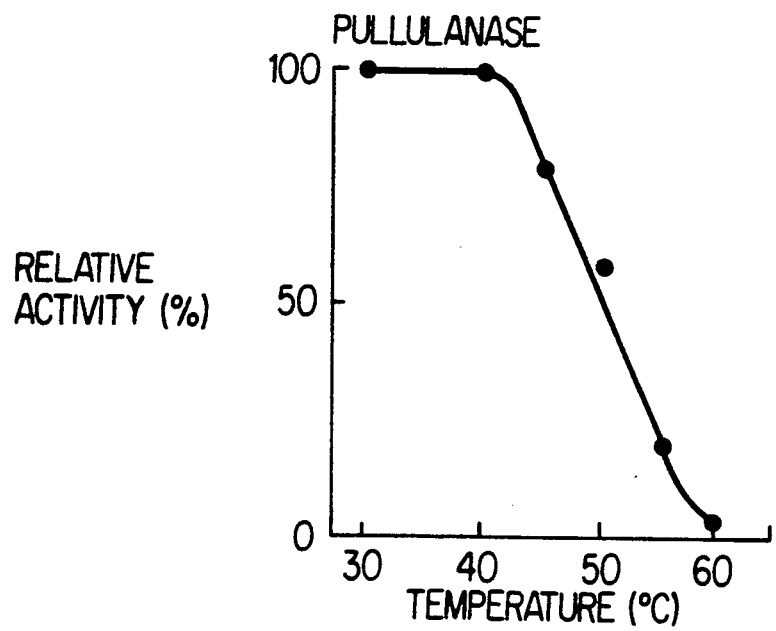
FIGS. 5(a) and 5(b) are drawings showing the relation of reaction temperature (at pH 9.5) vs. residual activity of the alkaline pullulanase Y having α-amylase activity of this invention.
Figure 5B:
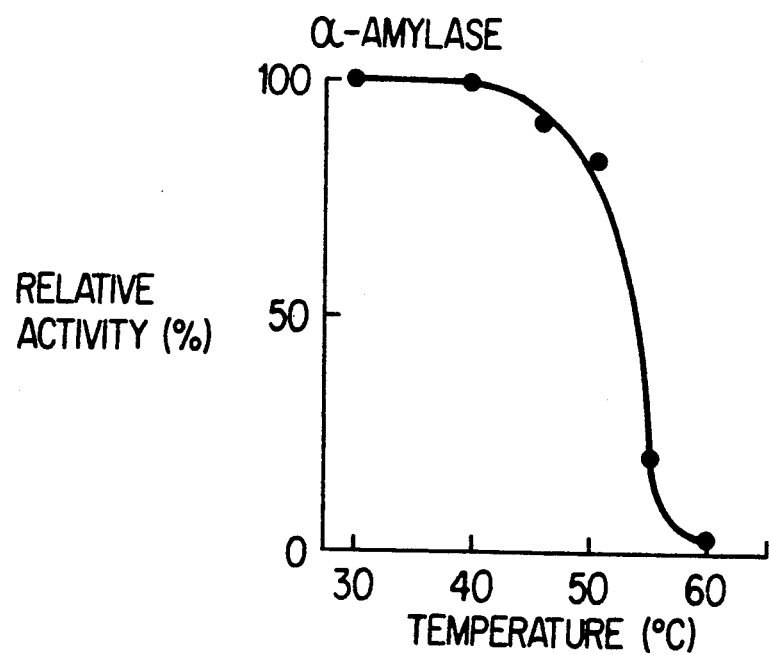

The temperature at which the enzyme loses its activity was examined by subjecting the enzyme to heat-treatment at various temperatures for 30 minutes at pH 9.5. Resultingly, the enzyme was stable up to 45° C. The results are shown in FIGS. 5(a) and 5(b).

(7) Molecular Weight

About 200,000±5,000, when measured by means of SDS-polyacrylamide gel electrophoresis (gel concentration: 7.5% w/v).

(8) Effects of Metal Ions

Pullulanase activity is adversely affected by $Hg^{2+}$, $Mn^{2+}$, and $Pb^{2+}$ ions and α-amylase activity is adversely affected by $Hg^{2+}$, $Mn^{2+}$, $Pb^{2+}$, $Cd^{2+}$, and $Zn^{2+}$ ions. Table 2 shows the results.

TABLE 2

Residual activity (%)

| Compound | Concentration | Pullulanase Activity | α-amylase Activity |
| --- | --- | --- | --- |
| No addition | — | 100 | 100 |
| Metal salt | | | |
| $HgCl_2$ | 1 mM | 36 | 53 |
| $MnCl_2$ | 1 mM | 51 | 28 |
| $PbCl_2$ | 1 mM | 53 | 53 |
| $CdCl_2$ | 1 mM | 80 | 38 |
| $ZnCl_2$ | 1 mM | 93 | 57 |
| Chelating agent | | | |
| EDTA | 10 mM | 77 | 17 (88)* |
| EGTA | 10 mM | 65 | 18 (91)* |

*The value in parenthesis is a residual activity when $Ca^{+2}$ ions was again added.

As shown in Table 2, the metal ions which adversely affect the pullulanase activity or the α-amylase activity of alkaline pullulanase of the present invention are different each other.

(9) Effects of Detergents 0.05% solution of a surfactant such as linear alkylbenzene sulfonate (LAS), sodium polyoxyethylene alkyl sulfate (ES), sodium α-olefin sulfonate (AOS), sodium α-sulfonated fatty acid ester (α-SFE), sodium alkyl sulfonate (SAS), sodium dodecyl sulfate (SDS), soaps and softanol was tested at 40° C. for 15 minutes to confirm no adverse effects on enzymatic activities.

(10) Effects of Chelating Agents

Chelating agents such as EDTA (10 mM), EGTA (10 mM) give no adverse effect on pullulanase activity, but heavily affects α-amylase activity. The α-amylase activity which has been adversely affected by a chelating agent can be restored by adding $Ca^{+2}$ ions as shown in Table 2.

(11) Resistance to Protease

In the presence of an alkaline protease, for example, Maxatase (IBIS), Sabinase (Novo), or the like in an amount of 0.2 AU/1, the activities were measured, to confirm that the enzyme of this invention exhibited strong resistance to any proteases.

As is clear from the above-mentioned enzymological characteristics, the alkaline pullulanase Y of this invention is an enzyme having physiologically and chemically different characteristics from conventional pullulanases having α-amylase activity.

In order to clarify the novelty of the enzyme of the present invention, comparison data on physiological and chemical characteristics of the alkaline pullulanase Y of the present invention and conventional pullulanases having α-amylase activity are shown in Table 3.

TABLE 3

| | Pullulanase | | |
| --- | --- | --- | --- |
| Microorganism | Japanese Patent Publication No. 18717/1989 *Bacillus subtilis* TU | Japanese Patent Laid-open No. 60376/1989 *Bacillus circulans* F-2 | Present Invention Bacillus sp. KSM-AP1378 |
| Optimum pH for Pullulanase activity | 7.0–7.5 | 7.0 | 8.5–10.0 |
| Optimum pH for α-amylase activity | 6.7–7.0 | 7.0–8.5 | 7.0–9.5 |
| Optimum temperature for Pullulanase activity | 50° C. | 50° C. | 50–55° C. |
| Optimum temperature for α-amylase activity | 60° C. | 50° C. | 45–50° C. |
| Molecular weight | 450,000 (gel filtration) | 218,000 (SDS electrophoresis) | 200,000 (SDS electrophoresis) |
| Major products from soluble starch* | G1, G2, G3 | G4, G5, G6 | G4, G5 |
| Major products from pullulan* | G3 | G3 | G3 |

*G1: glucose, G2: maltose, G3: maltotriose, G4: maltotetraose, G5: maltopentaose, G6: maltohexaose As is apparent from physicochemical and enzymological characteristics in Table 3, the alkaline pullulanase Y of the present invention is clearly different from a pullulanase-amylase complex produced by *bacillus subtilis* TU and an amylase having pullulanase activity produced by *Bacillus circulans* F-2.

Alkaline pullulanase Y of the present invention possesses α-amylase activity, and has an optimum pH at higher alkaline range than conventional alkaline pullulanases and exhibits excellent stability in a wide pH range. Further, alkaline pullulanase of the present invention has strong resistance to almost all detergent components such as surfactants, chelating agents, proteases for detergents, and the like.

Accordingly, the enzyme of the present invention can advantageously be used as a detergent component. The enzyme of the present invention has thus an outstanding utility in industrial fields.

Other features of the invention will become apparent in the course of the following description of the exemplary embodiments which are given for illustration of the invention and are not intended to be limiting thereof.

EXAMPLES

EXAMPLE 1

A spoonful of soil (about 0.5 g) of Tochigi-shi, Tochigi-ken, Japan was suspended in sterilized saline and the mixture was heat-treated at 80° C. for 15 minutes. A supernatant of the heat-treated mixture was appropriately diluted, applied onto an isolating agar medium (Medium A), and cultured at 30° C. for 3 days to grow colonies. The colonies which formed transparent zones in their peripheries due to pullulan dissolution were collected to obtain strains which produce pullulanase having α-amylase activity. These strains were inoculated into the liquid medium B and shake-cultured at 30° C. for 3 days. After cultivation, the cultured broth was centrifuged to separate a supernatant. The pullulanase and α-amylase activities of the supernatant were measured at pH 10 to select strains which produce alkaline pullulanase having α-amylase activity. Bacillus sp. KSM-AP1378 (FERM P-10886) which is a microorganism capable of producing alkaline pullulanase having α-amylase activity was thus obtained.

|  |  | % (w/v) |
|---|---|---|
| Medium A | Pullulan | 0.5 |
|  | Soluble starch | 0.5 |
|  | Colored Pullulan | 0.2 |
|  | Polypeptide | 0.2 |
|  | Yeast extract | 0.1 |
|  | $KH_2PO_4$ | 0.03 |
|  | $(NH_4)_2SO_4$ | 0.1 |
|  | $MgSO_4.7H_2O$ | 0.02 |
|  | $CaCl_2.2H_2O$ | 0.02 |
|  | $FeSO_4.7H_2O$ | 0.001 |
|  | $MnCl_2.4H_2O$ | 0.0001 |
|  | Agar | 1.5 |
|  | $Na_2CO_3$ | 0.5 |
|  | pH: 10.0 |  |
| Medium B | Pullulan | 0.5 |
|  | Soluble starch | 0.5 |
|  | Tryptone | 0.2 |
|  | Yeast extract | 0.1 |
|  | $KH_2PO_4$ | 0.03 |
|  | $(NH_4)_2SO_4$ | 0.1 |
|  | $MgSO_4.7H_2O$ | 0.02 |
|  | $CaCl_2.2H_2O$ | 0.02 |
|  | $FeSO_4.7H_2O$ | 0.001 |
|  | $MnCl_2.4H_2O$ | 0.0001 |
|  | $Na_2CO_3$ | 0.5 |
|  | pH: 10.0 |  |

EXAMPLE 2

The strains of Bacillus sp. KSM-AP1378 which produce the alkaline pullulanase Y having α-amylase activity were inoculated into the liquid medium B, which had the same composition as in Example 1, and shake-cultured at 30° C. for 3 days. After cultivation, cells were removed by means of centrifugation to obtain the preparation of crude pullulanase enzyme. The crude enzyme was processed according to a conventional method to prepare ethanol-dried powder. As a result, the alkaline pullulanase Y having α-amylase activity was obtained and confirmed as shown in Table 4. Enzymatic activity was measured at pH 9.

TABLE 4

| Strain | Amount of enzyme per 1 of medium (g) | Enzymatic activity (U/g) | |
|---|---|---|---|
|  |  | Pullulanase | α-amylase |
| KSM-AP1378 | 0.2 | 2,096 | 2,476 |

EXAMPLE 3

Bacillus sp. KSM-AP1378 capable of producing alkaline pullulanase having α-amylase activity was inoculated into a medium which had the same composition as the liquid medium B in Example 1 except that 1% of maltose was added instead of pullulan and soluble starch and shake-cultured at 30° C. for 2-3 days. Pullulanase activity of a supernatant after centrifugation was measured to be 211 U per one litter of the culture broth.

EXAMPLE 4

Figure 6:
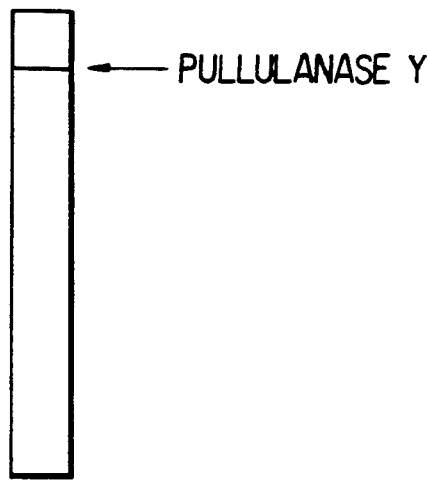
FIG. 6 is a drawing showing the results of electrophoresis of the alkaline pullulanase Y having α-amylase activity of this invention according to the method of Davis.

To a supernatant of the crude enzyme prepared in Example 2 was added DEAE cellulose powder and pullulanase in the supernatant was completely adsorbed to the DEAE cellulose. After 10 mM Tris-HCl buffer (pH 8) was used to wash the resin, the enzyme was eluted with 10 mM Tris-HCl buffer (pH 8) containing 0.6 M sodium chloride. The eluate was dialyzed against 10 mM Tris-HCl buffer. Then, the enzyme was adsorbed to α-cyclodextrin affinity column equilibrated with 10 mM Tris-HCl buffer and eluted with 10 mM Tris-HCl buffer (pH 8) containing β-cyclodextrin to collect active fractions. After dialyzing, the active fractions were adsorbed to DEAE Toyopeal 650S equilibrated with 10 mM Tris-HCl buffer (pH 8). The enzyme adsorbed was gradiently eluted with 10 mM Tris-HCl buffer containing sodium chloride having a concentration of 0.1–1 M to collect active fractions. After dialyzing, the active fractions were filled into a sephacryl S-200 column equilibrated with 10 mM Tris-HCl buffer (pH 8) containing 0.1 M sodium chloride and eluted with the same buffer containing 0.1 M sodium chloride to collect active fractions. The active fractions were concentrated on an ultrafiltration membrane and dialyzed overnight against 10 mM Tris-HCl buffer (pH 8) to obtain the alkaline pullulanase Y having α-amylase activity. The pullulanase Y having α-amylase activity obtained was subjected to electrophoresis using polyacrylamide gel (gel concentration: 15% w/v) according to the method of Davis [Ann. N.Y. Acad. Sci., 121, 404, (1964)], and stained with Coomassie Brilliant Blue to confirm that it gave a single band (see FIG. 6).

EXAMPLE 5

Figure 7:
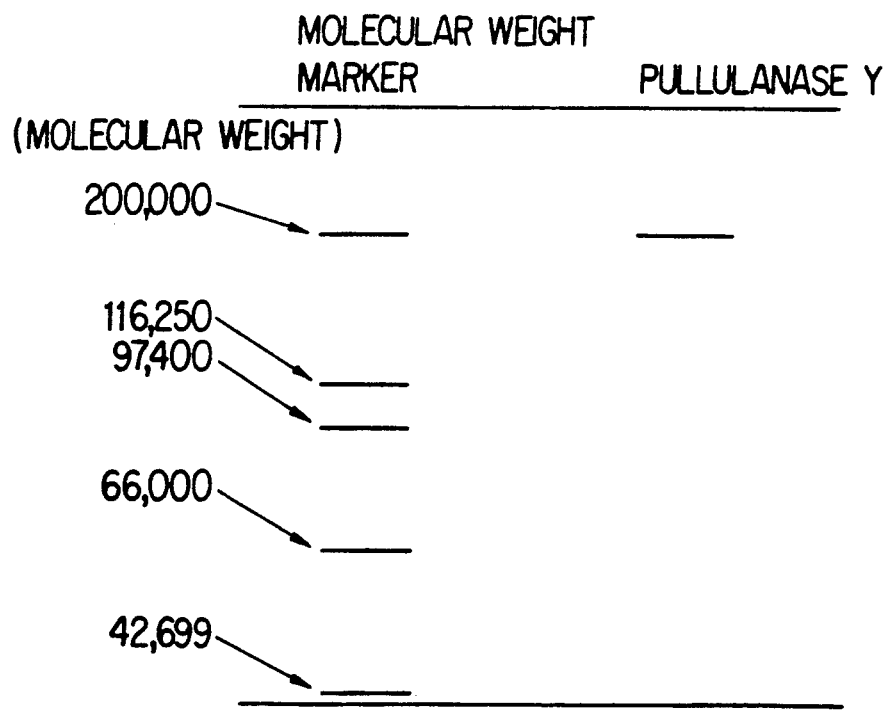
FIG. 7 is a drawing showing the results of SDS electrophoresis of the alkaline pullulanase Y having α-amylase activity of this invention.

The alkaline pullulanase Y having α-amylase activity obtained in Example 4 was subjected to sodium dodecyl sulfate (SDS) electrophoresis according to a conventional method to confirm that the enzyme had a molecular weight of 200,000±5,000. (See FIG. 7)

Obviously, numerous modifications and variations of the present invention are possible in light of the above teachings. It is therefore to be understood that the scope of the appended claims, the invention may be practiced otherwise than as specifically described herein.

What is claimed is:

1. An alkaline pullulanase Y having α-amylase activity which has an optimum pH range of 8.5-10 against pullulan and an optimum pH range of 7-9.5 against soluble starch, which possesses the following enzymological characteristics:
   (1) action
      acts on pullulan and soluble starch to produce mainly maltotriose from pullulan and mainly maltotetraose and maltopentaose from soluble starch, and acts also on glycogen to produce maltotetraose and maltopentaose;
   (2) substrate Specificity
      acts of pullulan, soluble starch, and glycogen;
   (3) working pH and Optimum pH Range
      has an active pH range on pullulan of 5-12 with an optimum pH range being 8.5-10, and has an active pH range on soluble starch of 4-12 with an optimum range being 7-9.5;
   (4) pH Stability
      is stable in a pH range of 6-10.5 against pullulan and in a pH range of 4-12 against soluble starch (treating condition: 45° C., 10 minutes);
   (5) working Temperature and Optimum Temperature
      acts on pullulan and soluble starch at wide temperatures ranging from 10° to 65° C. with an optimum temperature being around 50° C.;
   (6) thermal Stability
      is stable up to 45° C. when treated in a 10 mM glycine-NaCl-NaOH buffer (pH 9.5) for 30 minutes;
   (7) molecular Weight
      about 200,000±5,000, when measured by means of electrophoresis using sodium dodecyl sulfate (SDS);
   (8) effects of Metal Ions
      pullulanase activity is adversely affected by $Hg^{2+}$, $Mn^{2+}$, and $Pb^{2+}$ ions and α-amylase activity is adversely affected by $Hg^{2+}$, $Mn^{2+}$, $Pb^{2+}$, and $Zn^{2+}$ and $Cd^{2+}$ ions,
   said alkaline pullulanase Y being produced by a process comprising: culturing a microorganism producing an alkaline pullulanase having α-amylase activity, which is named as Bacillus sp, KSM-AP1378 and deposited as FERM P-10886 with Fermentation Research Institute, Agency of Industrial Science and Technology; and isolating the alkaline pullulanase Y having α-amylase activity from the cultured medium.

* * * * *

UNITED STATES PATENT AND TRADEMARK OFFICE
CERTIFICATE OF CORRECTION

PATENT NO. : 5,147,796
DATED : September 15, 1992
INVENTOR(S) : Katsutoshi Ara et al.

It is certified that error appears in the above-identified patent and that said Letters Patent is hereby corrected as shown below:

On Title Page:

Item [63], The Related U.S. Application Data should be as follows: --Continuation of Ser. No. 583,849, Sep. 13, 1990, abandoned--.

Signed and Sealed this

Twenty-sixth Day of October, 1993

Attest:

BRUCE LEHMAN

*Attesting Officer*    *Commissioner of Patents and Trademarks*